(12) United States Patent
Malaurie et al.

(10) Patent No.: US 8,663,105 B2
(45) Date of Patent: Mar. 4, 2014

(54) INGESTIBLE DEVICES FOR MEASURING PHYSIOLOGICAL PARAMETERS

(75) Inventors: Jean-Marie Malaurie, Mondeville (FR); Yvan Olivier Jean Ghislain Droinet, Douvres-la-Delivrande (FR); Marc-Herve Stodel, Reviers (FR)

(73) Assignee: NXP, B.V., Eindhoven (NL)

( * ) Notice: Subject to any disclaimer, the term of this patent is extended or adjusted under 35 U.S.C. 154(b) by 178 days.

(21) Appl. No.: 13/058,234

(22) PCT Filed: Aug. 8, 2009

(86) PCT No.: PCT/IB2009/053500
§ 371 (c)(1), (2), (4) Date: Aug. 23, 2011

(87) PCT Pub. No.: WO2010/018524
PCT Pub. Date: Feb. 18, 2010

(65) Prior Publication Data
US 2011/0295079 A1    Dec. 1, 2011

(30) Foreign Application Priority Data

Aug. 11, 2008    (EP) .................................... 08290765

(51) Int. Cl.
*A61B 5/00* (2006.01)
*A61B 5/07* (2006.01)
*H02J 7/00* (2006.01)
*H02J 7/34* (2006.01)

(52) U.S. Cl.
CPC ............... *A61B 5/073* (2013.01); *A61B 5/6861* (2013.01); *A61B 5/0002* (2013.01); *H02J 7/0031* (2013.01); *H02J 7/345* (2013.01); *A61B 5/6871* (2013.01); *A61B 5/6873* (2013.01); *Y10S 128/903* (2013.01); *Y10S 977/904* (2013.01)

USPC ........... 600/300; 600/302; 128/903; 320/166; 320/103; 335/4; 340/870.13; 340/870.39; 340/539.12; 977/904

(58) Field of Classification Search
None
See application file for complete search history.

(56) References Cited

U.S. PATENT DOCUMENTS 3,682,160 A * 8/1972 Murata ......................... 600/302
3,872,455 A    3/1975 Fuller et al.
5,572,108 A * 11/1996 Windes ......................... 320/167
5,748,103 A * 5/1998 Flach et al. ............... 340/870.07

(Continued)

FOREIGN PATENT DOCUMENTS

EP           1508296 A1       2/2005
JP        2005 130943 A       5/2005
WO      2006/116718 A2      11/2006

OTHER PUBLICATIONS

Arisha, K. et al. "System-Level Power Optimization for wireless Multimedia Communication"; Editors: Ramesh, K and Goodman, D.; Springer US; 2002, p. 21-40.*

(Continued)

*Primary Examiner* — Bill Thomson
*Assistant Examiner* — Marie Archer

(57) ABSTRACT

An ingestible apparatus produces and processes physiological signals representative of a physiological parameter. The apparatus measures the physiological parameter from within the body of a living entity. The apparatus includes a physiological transducer circuit to sense the physiological signals, a processor to process the physiological signals in response to the physiological transducer circuit, and a transmitter that transmits the processed signals during transmission intervals which are alternated with idle intervals. The apparatus further includes a capacitor-based circuit, including at least one capacitor, to accumulate sufficient charge during one of the idle intervals to supply power to the transmitter during one of the transmission intervals.

21 Claims, 2 Drawing Sheets

(56) References Cited

U.S. PATENT DOCUMENTS

Figure 1A:
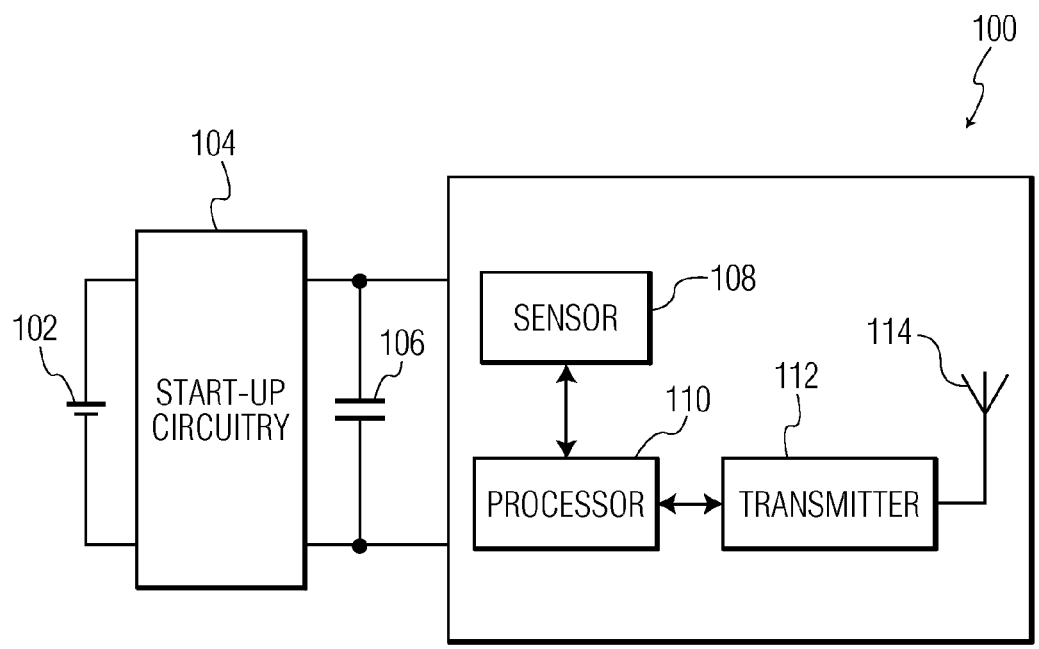

| | | | |
|---|---|---|---|
| 6,800,060 B2* | 10/2004 | Marshall | 600/309 |
| 7,273,454 B2* | 9/2007 | Raymond et al. | 600/301 |
| 8,038,599 B2* | 10/2011 | Kimoto et al. | 600/118 |
| 2002/0128542 A1* | 9/2002 | Van Over | 600/310 |
| 2003/0208244 A1* | 11/2003 | Stein et al. | 607/48 |
| 2004/0215084 A1 | 10/2004 | Shimizu et al. | |
| 2004/0225333 A1* | 11/2004 | Greatbatch et al. | 607/34 |
| 2005/0043601 A1* | 2/2005 | Kilcoyne et al. | 600/361 |
| 2005/0165317 A1* | 7/2005 | Turner et al. | 600/486 |
| 2005/0192489 A1* | 9/2005 | Marshall | 600/302 |
| 2007/0032839 A1* | 2/2007 | Parramon et al. | 607/60 |
| 2008/0146871 A1* | 6/2008 | Arneson et al. | 600/101 |
| 2008/0193139 A1* | 8/2008 | Bettesh | 398/128 |
| 2009/0187392 A1* | 7/2009 | Riskey et al. | 703/11 |

OTHER PUBLICATIONS

Chen, Z. et al.; "Self Organization and Energy Efficient TDMA MAC Protocol by Wake Up for Wireless Sensor Networks"; 2004; IEEE; p. 335-341.*

Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004.*

Lee, W.L. "Flexible-Schedule-Based TDMA Protocols for Supporting Fault-Tolerance, On-Demand TDMA Slot Transfer, and Peer-to-Peer Communication in Wireless Sensor Networks"; 2007; PhD Dissertation; p. 1-213.*

Miller, M. J. et al.;"On-Demand TDMA Scheduling for Energy Conservation in Sensor Networks", Technical Report; Jun. 2004; p. 1-10.*

Wegmuller, M. S.; "Intra-Body Communication for Biomedical Sensor Networks"; PhD dissertation; 2007; p. 1-173.*

NXP; "P89LPC935 Product Data Sheet"; 75 Pages (Nov. 26, 2008).

Hoskins, Seth, et al; "Near-Field Wireless Magnetic Link for an Ingestible Cattle Health Monitoring Pill"; Kansas State University; 4 Pages (2009).

International Search Report and Written Opinion for Application PCT/IB2009/053500 (Aug. 8, 2009).

* cited by examiner

INGESTIBLE DEVICES FOR MEASURING PHYSIOLOGICAL PARAMETERS

This patent document relates to an ingestible device for measuring a physiological parameter from within the body of a living entity, and more particularly, to a miniaturized temperature monitoring system applicable for swallow-able medical pills.

Ingestible pills may be used to monitor patient attributes from within a patient's body, for example, to replace or as an adjunct for implanted sensors or less accurate external sensors. Circuitry packaged inside a pass-through ingestible pill can be used for continuously monitoring certain patient attributes while the pill is still inside the patient. The characteristics of sensing and communication circuitry can often restrict the range of application. For example, sensing circuitry and communication generally requires the use of relatively large batteries to power the circuitry over the time period during which the pill is inside the patient, thus increasing the size of the pill.

Sensor monitoring and communication requirements may limit the useful sensing lifetime of the pill within the patient. Continuous measurement and transmission of information drains the power supply, which can result in a device becoming prematurely inactive prior to being expelled, particularly in those patients having gastric motility disorders.

Also, there may be difficulties associated with pill storage that can reduce the usable lifetime of such pills. Insufficient isolation of the power source from the sensing and communication circuitry during storage and prior to activation of such devices can drain the power supply, resulting in a reduced lifetime or premature device failure.

The present invention is directed to overcoming the above-mentioned challenges and others related to the types of applications discussed above and in other applications. These and other aspects of the present invention are exemplified in a number of illustrated implementations and applications, some of which are shown in the figures and characterized in the claims section that follows.

According to an example embodiment of the present invention, an ingestible apparatus produces and processes physiological signals representative of a physiological parameter. The apparatus measures the physiological parameter from within the body of a living entity. The apparatus includes a physiological transducer circuit to sense the physiological signals, a processor to process the physiological signals in response to the physiological transducer circuit, and a transmitter that transmits the processed signals during transmission intervals which are alternated with idle intervals. The apparatus further includes a capacitor-based circuit, including at least one capacitor, to accumulate sufficient charge during one of the idle intervals to supply power to the transmitter during one of the transmission intervals.

According to another example embodiment of the present invention, systems include one or more ingestible apparatuses as described above and a receiver unit to receive signals from the transmitter. In some embodiments, multiple ingestible apparatuses can be used to sense respective physiological parameters.

According to another example embodiment of the present invention, a method is provided for producing and communicating physiological signals representative of a physiological parameter. The physiological parameter is measured from within the body of a living entity using an ingestible apparatus. The method includes sensing the physiological signals, processing the physiological signals, powering the transmitter, and transmitting the processed signals during transmission intervals during which the transmitter is powered by a capacitor-based circuit. The method further includes disabling the transmitter and charging the capacitor during idle intervals that are alternated with the transmission intervals, the capacitor accumulating sufficient charge during one of the idle intervals to supply power to the transmitter during one of the transmission intervals.

The above summary is not intended to describe each illustrated embodiment or every implementation of the present invention.

Figure 1B:
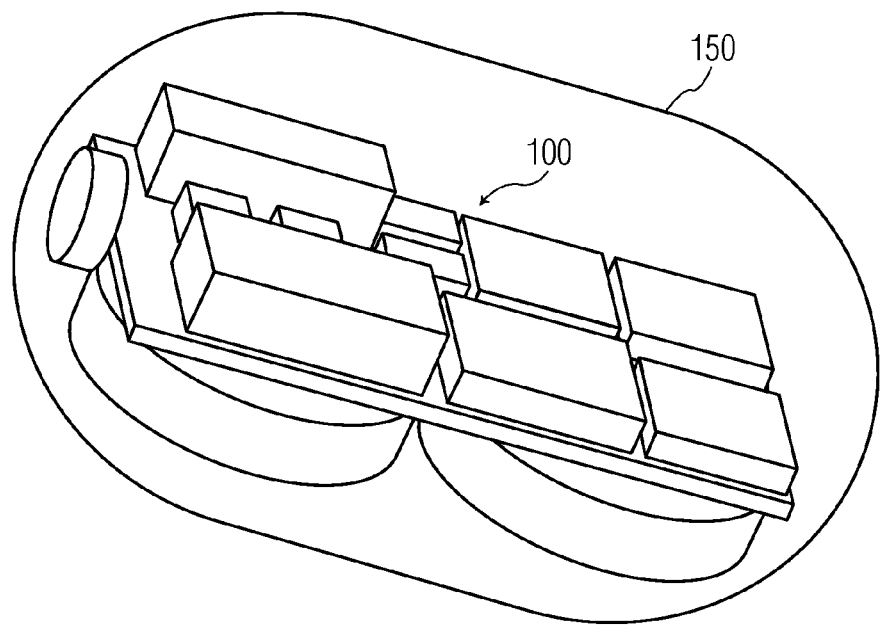
Figure 2:
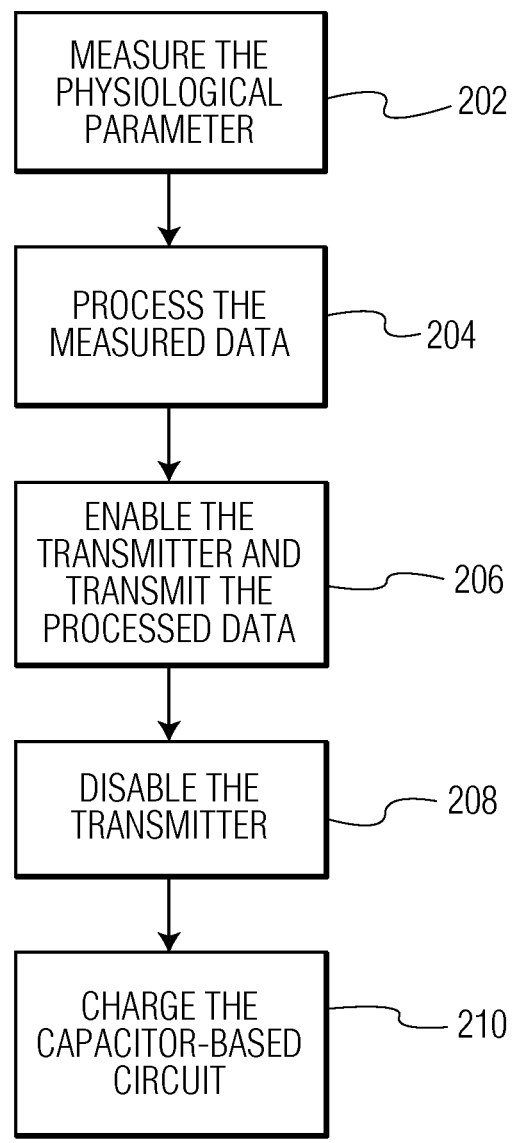

The invention may be more completely understood in consideration of the following detailed description of various embodiments of the invention in connection with the accompanying drawings, in which:

FIG. 1A schematically illustrates a block diagram of circuit in accordance with an example embodiment of the present invention;

FIG. 1B schematically illustrates an ingestible device in accordance with an example embodiment of the present invention; and FIG. 2 shows a flow chart of steps that may be performed in accordance with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention, including that defined by the claims.

The present invention is applicable to a variety of applications that make use of remote monitoring of physiological parameters, and particularly applicable to measuring temperature from within the body of a living entity. While the present invention is not necessarily limited to such applications, an appreciation of various aspects of the invention is best gained through a discussion of examples in such an environment.

According to an example embodiment of the present invention, an ingestible device produces and processes physiological signals representative of a physiological parameter. The device measures the physiological parameter from within the body of a living entity. The device is encased by an encapsulation that protects the device, thereby enabling it to be inserted into the body of the living entity for measuring and communicating signals representative of the physiological parameter over a period of time, for example, until the device is passed out of the body. In one implementation, the encapsulation is in the shape of a pill and the device is designed to be swallowed by the living entity, in which case the encapsulation is a material that is resistive to degradation by the digestive tract of the living entity and that is biocompatible with the living entity. The device includes a physiological transducer circuit that senses the physiological signals representative of a physiological parameter measured from within the body of a living entity. In one implementation, the physiological transducer circuit includes a temperature sensor that measures the temperature of the living entity, such as the SE95 digital temperature sensor from NXP Semiconductors, and a transmitter that transmits the measured temperature to the external receiver. In some implementations, additional physiological parameters may be measured by the same device or by multiple devices that transmit to the same receiver; for example, in communication bursts that are timed to mitigate against interference.

The device measures the physiological parameter and transmits this data during transmission intervals which are alternated with idle intervals during which the device is at least partially deactivated. The device further includes a capacitor-based circuit, including at least one capacitor, that supplies power to the transmitter during at least the transmission intervals, and that accumulates sufficient charge during one of the idle intervals to power the transmitter during one of the transmission intervals. In one implementation, the device includes a power supply, such as a battery, that is used to charge the capacitor during at least the idle intervals. The capacitor-based circuit is connected in parallel with the battery power supply and the capacitor-based circuit draws a small current from the battery power supply, thereby charging the capacitor-based circuit. The capacitor-based circuit supplies power during the transmission intervals when more current is required, which discharges the capacitor-based circuit. The device is operated in such a manner that the idle intervals are sufficiently longer than the measurement intervals to ensure that the capacitor-based circuit is sufficiently charged during one of the idle intervals to provide the transmitter with power during the next measurement interval.

FIG. 1A shows an apparatus 100 for measuring a physiological parameter from within the body of a living entity according to an example embodiment of the present invention. The apparatus 100 includes a battery 102 that is connected in parallel with start-up circuitry 104 and a capacitor-based circuit 106. For the purpose of illustration, the capacitor-based circuit 106 is shown in FIG. 1A as being a single capacitor; however, the capacitor-based circuit 106 can include multiple capacitors. The apparatus also includes a physiological transducer such as a sensor 108, a processor 110, a transmitter 112 and an antenna 114. In one implementation, the sensor 108 can measure various physiological parameters including, but not limited to, temperature, pressure and pH. In certain implementations, the apparatus 100 includes a separate sensor for measuring each physiological parameter, but for the sake of simplicity of illustration only one sensor 108 is shown in FIG. 1A. The apparatus 100 communicates with an external device (not shown) during transmission intervals. The capacitor 106 supplies power to the transmitter 112 during the transmission intervals and the capacitor is recharged by the battery 102 between transmission intervals.

The apparatus 100 is surrounded by an encapsulation 150, which is shown in FIG. 1B as being shaped like a pill. In one implementation, the apparatus 100 (including the encapsulation 150) is sufficiently sized such that it can be easily swallowed by a person. One of skill in the art will recognize that the present invention is not limited to a device of such a size and shape or for use only in people. For example, the device of present invention could be a variety of different sizes and shapes, and the device could be used in a wide variety of different types of living entities such as farm animals and lab animals. In one implementation, the encapsulation 150 is polycarbonate. The encapsulation 150 can be a single piece of material or it can be formed from two or more pieces of material that are assembled with biocompatible glue. In another implementation, the encapsulation is covered with a parylene coating. In a further implementation, the encapsulation 150 is a hollow capsule that contains the apparatus 100 and the capsule is filled with a biocompatible gel or resin.

In one implementation, the battery 102 has a large internal resistance such that it supplies a current that is too small to provide power to the sensor 108 and the transmitter 112, whereas the capacitor 106 has a sufficiently low internal resistance to supply power to the sensor and the transmitter.

The capacitor 106 can, for example, have a capacitance of 220 μF. In one implementation, the capacitor 106 is a tank capacitor. The battery can be, for example, a 337 button cell battery available from various companies including Energizer and Sony, and the apparatus 100 can include one or more of these batteries. When the apparatus is in the operating mode, the capacitor 106 draws a small current from the battery 102 which charges the capacitor. During the transmission intervals, when more current is required (e.g., about 1 to 25 mA), the capacitor 106 supplies this current and is discharged. The capacitor 106 is then recharged from the battery 102 prior to the next transmission interval. The sensor 108 and the transmitter 112 can be deactivated in between transmission intervals.

In one implementation, the processor 112 is a microcontroller that has a real time clock system to sequence the transmission intervals, such as the P89LPC935 from NXP Semiconductors. The power consumption between two transmission intervals is reduced to a few microamperes, allowing the apparatus to function for an extended period of time before that battery 102 is depleted.

In certain implementations, the power consumption of the apparatus 100 is decreased using a smart enable. The processor 110 enables various parts of the apparatus 100, such as the sensor 108 and the transmitter 112, only when their functions are being used. The sensor 108 and the transmitter 112 are switched off or operated in power-down mode when they are not in use. For example, the sensor's power supply line can be switched via a MOS transistor allowing it to be disabled when not in use, and internal blocks of the transmitter 112 can be enabled by the processor 110 only when required. Moreover, other low power modes that are used by a smart software implementation further reduce power consumption; for example, there is short period of time between the start of the temperature sensor operation and the time the measurement is stable, so the processor 110 can delay activation of the transmitter 112 until an accurate temperature measurement is obtained. The processor 110 can also operate in a low-power mode during the time periods between transmission intervals when the capacitor 106 is being charged. The reduced power consumption allows for the use of a small battery 102, which enables the apparatus 100 to be placed in a pill shaped encapsulation 150 that can be swallowed by a person. For example, the pill can have a diameter of about 8 mm and a length of about 17 mm.

The operation of the start-up circuitry 104 will now be described. The start-up circuitry 104 allows the apparatus 100 to be stored for a significant period of time (e.g., at least several months), without resulting in a significant loss of operating time, by enabling the apparatus to fully stop power consumption. During storage, the apparatus 100 is completely turned off to prevent depletion of the battery 102. An external RF start signal is generated to enable the apparatus 100. The apparatus 100 detects the external RF start signal, thereby causing the apparatus to switch to the operation mode. The RF start signal transfers some power to the start-up circuit 104 through inductive coupling, thereby enabling the processor 110. For example, the RF start signal transfers sufficient power to the start-up circuit 104 to switch-on a MOS transistor, which causes the battery 102 to begin supplying power to the capacitor 106. When sufficient charge has accumulated on the capacitor 106 to supply power to the processor 110, the processor generates an internal power-on reset that starts apparatus 100. The apparatus 100 then becomes fully under control of the processor 110. The processor is also capable of shutting down the apparatus and returning it to the storage mode in which power consumption is fully stopped. In one implementation, the transmitter 112 is a transceiver that also includes a receiver. The apparatus 100 can receive instructions, such as a power-down instruction, from an external device in this case.

According to another embodiment of the present invention, a plurality of ingestible devices, such as apparatus 100 of FIG. 1A, can be used in combination with an external receiver. Each of the devices communicates with the external receiver according to a communications time schedule such as time division multiple access (TDMA). The devices are each assigned a predetermined time schedule during which they measure a physiological parameter from within the body of a living entity, and transmit the measured data to the external receiver. The transmission schedules of the devices are such that only one of the devices communicates with the external receiver. The devices can include an identification signal as part of the data transmitted to the external receiver in order to identify the device that is providing the data. The time schedules themselves can also be used to identify the device that transmitted the data since the devices transmit at predetermined times and only one device is transmitting at a given time. In one implementation, all of the devices are placed with the body of the same living entity. In this case, the devices could all be used to measure the same physiological parameter or each device could be used to monitor a different physiological parameter. In another implementation, the devices could each be placed within the bodies of different living entities, thereby enabling a single receiver to be used to monitor physiological parameters of multiple living entities.

FIG. 2 shows a flow chart of a method of producing and communicating signals representative of a physiological parameter measured from within the body of a living entity, according to an example embodiment of the present invention. An ingestible apparatus, such as apparatus 100 of FIG. 1A, is used to produce and communicate the signals. The ingestible apparatus includes a sensor that measures the physiological parameter, a processor that processes the measured data, a transmitter, and a capacitor. The method includes measuring the physiological parameter in step 202. The measured data is then processed in step 204. The transmitter is then enabled in step 206 by providing power to the transmitter from the capacitor and the processed data is transmitted by the apparatus. The transmitter is enabled during transmission intervals that alternate with idle intervals during which the transmitter is disabled. The transmitter is then disabled during the idle intervals in step 208. In one implementation, the sensor is also enabled during the transmission intervals and disabled during the idle intervals. The capacitor is then charged during the idle intervals in step 210. The capacitor accumulates sufficient charge during one of the idle intervals to supply power to the transmitter during one of the transmission intervals.

In addition to the above, the various processing approaches described herein can be implemented using a variety of devices and methods, including general purpose processors implementing specialized software, digital signal processors, programmable logic arrays, discrete logic components and fully-programmable and semi-programmable circuits such as PLAs (programmable logic arrays). For example, the above algorithms are executed on a microprocessor in connection with certain embodiments, and may be implemented as part of one or more of the devices shown in the figures.

The various embodiments described above and shown in the figures are provided by way of illustration only and should not be construed to limit the invention. Based on the above discussion and illustrations, it will be recognized that the circuits described herein may be manufactured using standard processes and techniques. Those skilled in the art will readily recognize that various modifications and changes may be made to the present invention without strictly following the exemplary embodiments and applications illustrated and described herein. Such modifications and changes do not depart from the true scope of the present invention.

What is claimed is:

1. An ingestible apparatus for producing and processing physiological signals, the ingestible apparatus comprising:
   a physiological transducer circuit configured to sense physiological signals representative of a physiological parameter measured from within a body of a living entity;
   a processor, responsive to the physiological transducer circuit, that is configured to process the physiological signals to produce processed signals;
   a transmitter configured to transmit the processed signals during transmission intervals which are alternated with idle intervals;
   a capacitor-based circuit, including at least one capacitor, configured to accumulate sufficient charge during one of the idle intervals to supply power to the transmitter during one of the transmission intervals;
   a power supply; and
   startup circuitry responsive to an external RF signal configured to permit flow of charge from the power supply to the capacitor-based circuit.

2. The ingestible apparatus of claim 1, further comprising:
   an encapsulation structure configured to secure therein the physiological transducer circuit, the processor, the transmitter, and the capacitor-based circuit.

3. The ingestible apparatus of claim 2, wherein the encapsulation structure is pill shaped and has outer dimensions of about 8 mm in diameter and about 17 mm in length.

4. The ingestible apparatus of claim 1, wherein the capacitor-based circuit includes a tank capacitor.

5. The ingestible apparatus of claim 1, further comprising:
   an encapsulation structure configured to secure therein the physiological transducer circuit, the processor, the transmitter, and the capacitor-based circuit, wherein the capacitor-based circuit includes a tank capacitor.

6. The ingestible apparatus of claim 1, wherein the power supply includes a battery.

7. The ingestible apparatus of claim 1, wherein the transmission intervals are at least an order of magnitude shorter than the idle intervals.

8. The ingestible apparatus of claim 1, wherein the physiological transducer circuit senses the physiological parameter during the transmission intervals, the capacitor-based circuit further accumulating sufficient charge during one of the idle intervals to supply power to the physiological transducer circuit during one of the transmission intervals.

9. The ingestible apparatus of claim 1, wherein the apparatus is adapted to be swallowed by a human being.

10. The ingestible apparatus of claim 1, wherein the physiological transducer circuit includes a temperature sensor.

11. The ingestible apparatus of claim 1, wherein the physiological parameter is one of temperature, pressure, and pH.

12. The ingestible apparatus of claim 1, wherein the transmitter transmits communication bursts in accordance with a communication time schedule.

13. The ingestible apparatus of claim 12, wherein the communication time schedule is Time Division Multiple Access (TDMA).

14. The ingestible apparatus of claim 1, in which the startup circuit is arranged to prevent charging of the capacitor-based circuit and operation of the processor prior to activation of the apparatus.

15. The ingestible apparatus of claim 1, wherein the physiological transducer circuit and the transmitter are deactivated during the idle intervals.

16. A method for producing and communicating a physiological parameter measured from within a body of a living entity using an ingestible apparatus that includes a physiological transducer circuit that senses physiological signals representative of the physiological parameter, a processor that produces and processes the physiological signals, a transmitter, and a capacitor-based circuit, the method comprising:

sensing the physiological signals by measuring the physiological parameter from within the body of the living entity;

processing the physiological signals to produce processed signals;

powering the transmitter and transmitting the processed signals during transmission intervals during which the transmitter is powered by the capacitor-based circuit;

disabling the transmitter and charging the capacitor-based circuit responsive to an external RF signal during idle intervals that are alternated with the transmission intervals, the capacitor-based circuit accumulating sufficient charge from a power supply during one of the idle intervals to supply power to the transmitter during one of the transmission intervals; and under control of the processor, shutting down the apparatus and returning it to a storage mode in which power consumption is fully stopped.

17. The method of claim 16, further comprising:
disabling the transmitter and the physiological transducer circuit during each of the idle intervals.

18. A system for producing and processing physiological signals, the system comprising:

a receiver unit; and at least one ingestible apparatus that further comprises:

a physiological transducer circuit configured to sense physiological signals representative of a physiological parameter measured from within a body of a living entity;

a processor, responsive to the physiological transducer circuit, that is configured to process the physiological signals to produce processed signals;

a transmitter configured to transmit the processed signals during transmission intervals which are alternated with idle intervals; and a capacitor-based circuit, including at least one capacitor, configured to accumulate sufficient charge during one of the idle intervals to supply power to the transmitter during one of the transmission intervals;

a power supply; and startup circuitry responsive to an external RF signal arranged to permit flow of charge from the power supply to the capacitor-based circuit.

19. The system of claim 18, further comprising:
two or more of the ingestible apparatuses, each configured to sense respective physiological signals representative of respective physiological parameters.

20. The system of claim 19, wherein each of the two or more ingestible apparatuses is configured to transmit respective physiological signals according to different time schedules.

21. The system of claim 19, wherein each of the two or more ingestible apparatuses transmit a different apparatus identification.

* * * * *